United States Patent [19]

Fritz et al.

[11] 4,240,819
[45] Dec. 23, 1980

[54] METHOD FOR THE INHIBITION OF PLANT GROWTH

[75] Inventors: Charles D. Fritz, Hatfield, Pa.; Wilbur F. Evans, Kuala Lumpur, Malaysia; Anson R. Cooke, Hatfield, Pa.

[73] Assignee: Union Carbide Agricultural Products, Inc., Ambler, Pa.

[21] Appl. No.: 221,803

[22] Filed: Jan. 28, 1972

Related U.S. Application Data

[60] Division of Ser. No. 869,386, Oct. 24, 1969, which is a continuation-in-part of Ser. No. 693,698, Dec. 27, 1967, abandoned, which is a continuation-in-part of Ser. No. 617,860, Feb. 23, 1967, abandoned.

[51] Int. Cl.³ .............................................. A01N 57/20
[52] U.S. Cl. ............................................ 71/76; 71/86; 71/89
[58] Field of Search ............................................ 71/86

[56] References Cited

U.S. PATENT DOCUMENTS

| 3,531,549 | 9/1970 | Randall | 71/86 |
| 3,551,528 | 12/1970 | Randall | 71/86 |
| 3,600,435 | 8/1971 | Randall et al. | 71/86 |

*Primary Examiner*—Glennon H. Hollrah
*Attorney, Agent, or Firm*—Robert C. Brown; Dale Lynn Carlson

[57] ABSTRACT

A method for the inhibition of plant growth which comprises applying thereto an effective amount of 2-chloroethylphosphonic acid.

1 Claim, No Drawings

METHOD FOR THE INHIBITION OF PLANT GROWTH

This invention relates to the use of 2-chloroethylphosphonic acid in order to inhibit plant growth and this is a division of Application Ser. No. 869,386, filed Oct. 24, 1969 and entitled "Growth Regulation Process", which in turn was a Continuation-In-Part Application based on prior co-pending Application Ser. No. 693,698, filed Dec. 27, 1967 and entitled "Phosphonic Compound Growth Regulation Process", now abandoned, which in turn was a Continuation-In-Part Application based on prior co-pending Application Ser. No. 617,860, filed Feb. 23, 1967 and entitled "Growth Regulation Process Utilizing Phosphonic Compounds", now abandoned.

The induction of an ethylene response in plant growth by other means has been known for some time in the art. See "Plant Biochemistry" by James Bonner and J. E. Varner (1965), pages 641 to 664.

A fairly well known ethylene response is the use of gaseous ethylene in the ripening of bananas which has been carried out on a commercial scale for many years. It is also known to employ ethylene in essentially gaseous form to stimulate flower initiation in pineapples. See "Hormonal Control of Plant Growth" by N. S. Parihar (1964), pages 69 to 79. Here, ethylene was applied on a commercial scale using cumbersome equipment to drench the pineapple plants with ethylene-saturated liquid. Similar, but less powerful effects on plant tissues have been caused by other unsaturated hydrocarbic gases.

The mechanism by which ethylene and the other gases affect the growth cycle of plants is far from fully understood, but it is clear that they do play a role. It will be seen that the phosphonic acid compound used to practice the present invention contains, in its structure, molecular configurations which are capable of breaking down into ehtylene or like compounds, although there is no intention to limit the present invention to this theory or any other theory.

The use of certain other phosphonate compounds in the agricultural art is known for herbicidal purposes as set forth in U.S. Pat. Nos. 2,927,014 and 3,223,514. However, it will be seen that the compounds disclosed in the aforesaid two patents do not produce the growth regulating responses for ethylene-type response of the present invention.

Instead, the present invention involves inhibition of plant growth through the application of 2-chloroethylphosphonic acid at the plant site.

Reference is hereby made to the following prior co-pending applications, the disclosures of which are hereby incorporated by reference:

(1) Application Ser. No. 617,860
Filed: Feb. 23, 1967, now abandoned
Inventors: Charles D. Fritz and Wilbur F. Evans
Title: Growth Regulation Process Utilizing Phosphonic Compounds (2) Application Ser. No. 617,820 (GAF Case 1752) U.S. Pat. No. 3,531,549 and Ser. No. 617,819 (GAF Case 1753) U.S. Pat. No. 3,551,528
Both Filed: Feb. 23, 1967
Inventor: David I. Randall
Title of Both: Phosphonic Acid Esters and Method for their Preparation
Assignee: General Aniline and Film Corporation The foregoing applications specified hereinabove disclose preparation techniques for 2-chloroethylphosphonic acid.

Certain preliminary details connected with the inhibition of plant growth should make for a better appreciation of the invention.

2-chloroethylphosphonic acid used in the method of the present invention is soluble in water and can be applied to plants in aqueous solutions composed wholly or partially of water. Partial solutions include those formed of water and, for instance, acetone or methyl ethyl ketone. Any liquid medium may be used, provided that it is not toxic to the plant.

As will be demonstrated in connection with certain examples in this specification, 2-chloroethylphosphonic acid, of the present invention, has been quite effective in the inhibition of plant growth in connection with a wide variety of plant species at various concentrations of active phosphonic acid compounds. Amounts of as little as 0.1 lb./acre of 2-chloroethylphosphonic acid has been observed to cause marked increase in branching and lateral growth of several varieties of tomato plants. Moreover, compounds used in the process of this invention, when employed at concentrations ranging from 0.1 lb. to 16 lbs./acre (or from 10 to 48,000 p.p.m.) have demonstrated pronounced inhibition of plant growth.

The precise amount of 2-chloroethylphosphonic acid will depend upon the particular plant species being treated. An amount of from about 0.1 lb. to as much as 25 lbs. to 30 lbs./acre of these compounds, when applied to plants, will result in varying inhibition of plant growth depending upon the total amount of compound used, as well as the particular plant species being treated. Of course, the amount of 2-chloroethylphosphonic acid should be nonphytotoxic with respect to the plant being treated.

It is preferred that the compound used in the process of the present invention be applied at rates of $\frac{1}{2}$ to 4 lbs./acre in aqueous solution and that the application rate, in terms of total volume, varies from about 1 to 100 gallons per acre.

The 2-chloroethylphosphonic acid used in the process of this invention is generally soluble in water. However, if desired, the compound used in the process of this invention may be absorbed onto solid carriers, such as vermiculite, attaclay, talc and the like for application via a granular vehicle. Application of water thin solutions or solids is accomplished using conventional equipment that is well known in the art.

Although the preferred method of application of the compound used in the process of this invention is directly to the foliage and stems of plants, it has been found that the compound may be applied to the soil in which the plants are growing, and that such compound will be root-absorbed to a sufficient extent so as to result in the inhibition of plant growth in accordance with the teachings of this invention.

The compound used in the process of the present invention is preferably applied to growing plants, as set forth in the examples in this specification.

The compound which is usable in the process of the present invention may be prepared in accordance with said previously mentioned Application Ser. No. 617,820, entitled "Phosphonic Acid Esters and the Method for their Preparation", (Case 1752), the entire disclosure of which is hereby incorporated by reference, as applicable to 2-chloroethylphosphonic acid.

In order to illustrate the surprising results flowing from this invention, there are presented below a series of experimental test results which are presented solely by way of illustration and are in no way intended to be construed as in any way limiting the scope of this invention.

It has been theorized that with the practice of the present invention, the 2-chloroethylphosphonic acid breaks down outside the plant while still in the aqueous solution in which it was applied, and that the ethylene thus released is assimilated by the plant in gaseous form. However, this seems unlikely since, even when stabilized, against hydrolytic breakdown, the phosphonic acid will, to a greater or lesser extent, exert plant growth regulating activity when applied to plants, as demonstrated, for instance, by the epinasty tests upon tomato plants.

It is therefore theorized that the phosphonic acid used in the practice of the present invention exerts its inhibition of plant growth, at least in the great majority of cases, by assimilation into the metabolic system of the plant. Indeed, analytical investigations have shown that immediately following application to the plant, residues of the phosphonic acid are, for a limited period of time, to be found in plant tissues. Other investigations have shown that in many plants, some time after the application of the phosphonic acid, the plant tissues contain detectable amounts of ethylene.

From the foregoing it can be concluded that the phosphonic acid is broken down within plant tissue to release ethylene, and that the ethylene thus released exerts its normal functions. Indeed, it appears that the amount of ethylene released within the plant tissue is greater than that which could be derived from the phosphonic acid assimilated by the plant tissues. If this is correct, then it would seem to follow that the assimilation of the phosphonic acid by the plant tissues may trigger-off the enzymatic or other systems within the plant which in themselves generate ethylene.

The foregoing explanation is presented in an effort to promote a better understanding of the present invention, but since other investigations are still being carried out, it is quite possible that additional observations may necessitate a revision or even an abandonment of such a theory. In recognition of this, it is again repeated that the reasons why the present invention has proved to be so successful have not as yet been determined with certainty, and this specification is to be so understood.

EXAMPLE 1

This evaluation demonstrates the use of a compound of the invention to control growth.

Corn (Zea sp.) plants were sprayed at the eight-leaf stage with aqeuous solutions of 2-chloroethylphosphonic acid. The results are recorded below.

| Treatment rate lb/A | 3 Months after application % height reduction | Increase in number of brace roots reaching soil surface |
|---|---|---|
| Control | 0 | — |
| 0.25 | 13 | 0 |
| 0.50 | 14 | 1 |
| 1.0 | 17 | 3 |
| 2.0 | 23 | 3 |
| 4.0 | 39 | 4 |

Distance of ear from the soil surface to the ear tip was reduced with all treatments. Organ primordia (tissue in the stem which develops into roots, leaves or fruit) was stimulated as evidenced by increased numbers of brace roots from the stem reaching the soil surface.

EXAMPLE 2

This evaluation demonstrates the use of a compound of the invention to reduce plant height.

Cotton plants (*Gossypium hirsutum*) were sprayed, when squares (the bolls) were just forming, with aqueous solutions of 2-chloroethylphosphonic acid. The following results were recorded ten weeks later.

| Treatment Rate kg/Ha | Bolls/Plant | Change in plant height |
|---|---|---|
| Control (0) | 19.1 | — |
| 1.12 | 29.3 | +2% |
| 2.24 | 24.7 | −12% |
| 4.48 | 26.0 | −13% |

This increased yield of cotton is apparent. The reduction in plant height is useful, being indicative of a general reduction of non-useful vegetation.

EXAMPLE 3

This evaluation demonstrates the use of a compound of the invention for control of vegetative growth.

Cucumber (cucumis sp.) varieties Wisconsin SMR 18 (monoecious) and variety Lemon (andromonecious) where sprayed with aqueous solutions of 2-chloroethylphosphonic acid and gibberellic acid at the first to third true leaf stage of vegetative development. The results are recorded below.

| Treatment | Rate ppm | Length of first internode (cm) | Node of first flower Female or perfect | Node of first flower Male | Number of flowers on first 10 nodes Female or perfect | Number of flowers on first 10 nodes Male |
|---|---|---|---|---|---|---|
| WISCONSIN SMR 18 | | | | | | |
| Control | 0 | 7.7 ± 0.6 | 8.0 ± 0.5 | 2.0 ± 0.0 | 2.0 ± 0.0 | 33.4 ± 1.8 |
| Gibberellic acid | 2000 | 16.0 ± 0.7 | ** | 1.3 ± 0.3 | 0.0 | 33.0 ± 4.3 |
| 2-chloroethyl-phosphonic acid | 250 | 3.7 ± 0.2 | 2.0 ± 0.0 | 14.3 ± 0.5 | 14.0 ± 1.7 | 0.0 |
| Gibberellic acid + 2-chloroethyl-phosphonic acid | 2000 + 250 | 10.9 ± 0.6 | 3.0 ± 0.5 | 7.0 ± 0.5 | 4.0 ± 0.5 | 8.3 ± 2.0 |

-continued

| Treatment | Rate ppm | Length of first internode (cm) | Node of first flower | | Number of flowers on first 10 nodes | |
|---|---|---|---|---|---|---|
| | | | Female or perfect | Male | Female or perfect | Male |
| | | | LEMON | | | |
| Control | 0 | 4.6 ± 0.5 | ** | 3.0 ± 0.0 | 0.0 | 26.6 ± 0.5 |
| Gibberellic acid | 2000 | 8.3 ± 0.3 | ** | 5.7 ± 0.7 | 0.0 | 18.0 ± 1.6 |
| 2-chloroethyl-phosphonic acid | 250 | 3.0 ± 0.2 | 8.0 ± 0.5 | 11.7 ± 1.9 | 4.0 ± 0.8 | 2.3 ± 4.1 |

Number of plants for internode length measurements 12 days after treatment.
**No female or perfect flowers on first 17 nodes.

The effects of 2-chloroethylphosphonic acid on vegetative growth inhibition were also antagonized by gibberellic acid. Gibberellic acid is known to stimulate male sex expression and stimulate vegetative growth. Vegetative growth inhibition is evidenced by shortening of the internodes as this will allow closer spacing and higher populations and consequently higher yields per acre.

EXAMPLE 4

This evaluation demonstrates the use of a compound of the invention for controlling vegetative growth.

Grape (Vitis sp.) vines were sprayed during the vegetative growth periods with aqueous solutions of 2-chloroethylphosphonic acid. The results are recorded below.

| Treatment rate pm | % Vegetative growth inhibition | | |
|---|---|---|---|
| | July spray | August spray | September spray |
| Control | 0 | 0 | 0 |
| 125 | 25 | 20 | 23 |
| 250 | 35 | 30 | 32 |
| 500 | 60 | 65 | 67 |
| 1000 | — | — | 89 |

Inhibiting vegetative growth is of economic value to reduce the amount of vine pruning required and to allow sunlight to penetrate the vines which is important for quality fruit ripening. The September spray was of particular value for accelerating senescence.

Without further elaboration, the foregoing will so fully illustrate our invention, that others may, by applying current or future knowledge, readily adapt the same for use under various conditions of service.

What is claimed as the invention is:

1. A method for the inhibition of plant growth which comprises applying thereto an effective amount of 2-chloroethylphosphonic acid.

* * * * *